United States Patent
Davies et al.

(10) Patent No.: US 9,585,634 B2
(45) Date of Patent: *Mar. 7, 2017

(54) ULTRASOUND CATHETER WITH ROTATABLE TRANSDUCER

(71) Applicant: Volcano Corporation, San Diego, CA (US)

(72) Inventors: Stephen Charles Davies, Folsom, CA (US); Norman Hugh Hossack, Folsom, CA (US)

(73) Assignee: Volcano Corporation, San Diego, CA (US)

(*) Notice: Subject to any disclaimer, the term of this patent is extended or adjusted under 35 U.S.C. 154(b) by 595 days.

This patent is subject to a terminal disclaimer.

(21) Appl. No.: 13/663,089

(22) Filed: Oct. 29, 2012

(65) Prior Publication Data

US 2013/0060145 A1    Mar. 7, 2013

Related U.S. Application Data

(63) Continuation of application No. 12/351,368, filed on Jan. 9, 2009, now Pat. No. 8,317,713.

(51) Int. Cl.
*A61B 8/14*    (2006.01)
*A61B 8/00*    (2006.01)
*A61B 8/12*    (2006.01)

(52) U.S. Cl.
CPC .............. *A61B 8/4461* (2013.01); *A61B 8/12* (2013.01); *A61B 8/445* (2013.01); *A61B 8/4483* (2013.01)

(58) Field of Classification Search
CPC ................. A61B 8/12; A61B 8/4461
USPC ........................................... 600/466
See application file for complete search history.

(56) References Cited

U.S. PATENT DOCUMENTS

| | | | |
|---|---|---|---|
| 4,462,255 A * | 7/1984 | Guess et al. .................... | 73/633 |
| 4,515,017 A | 5/1985 | McConaghy | |
| 5,090,414 A | 2/1992 | Takano | |
| 5,348,017 A | 9/1994 | Thornton et al. | |
| 5,373,849 A * | 12/1994 | Maroney et al. ............. | 600/463 |
| 5,377,682 A | 1/1995 | Ueno et al. | |
| 5,842,994 A * | 12/1998 | TenHoff et al. .............. | 600/466 |

(Continued)

FOREIGN PATENT DOCUMENTS

| | | |
|---|---|---|
| JP | 5-29600 | 4/1993 |
| JP | 5-95595 | 12/1993 |

(Continued)

OTHER PUBLICATIONS

Supplementary European Search Report received in European Patent Application No. 09838026.4, dated Nov. 29, 2012, 7 pages.

(Continued)

*Primary Examiner* — Tse Chen
*Assistant Examiner* — Hien Nguyen
(74) *Attorney, Agent, or Firm* — Haynes and Boone, LLP (57) ABSTRACT

An ultrasound catheter assembly having a rotatable transducer assembly is disclosed. The ultrasound catheter assembly includes an elongate flexible shaft having a lumen and a proximal end and a distal end. The catheter assembly further includes a drive member that engages the transducer assembly at a distal end of the catheter. Rotation of the drive member in a first direction causes the transducer assembly to rotate in an oscillatory fashion in a second direction.

18 Claims, 5 Drawing Sheets

(56) References Cited

U.S. PATENT DOCUMENTS

| | | | |
|---|---|---|---|
| 6,423,002 | B1 | 7/2002 | Hossack |
| 6,905,466 | B2 | 6/2005 | Salgo et al. |
| 7,033,320 | B2 | 4/2006 | Von Behren et al. |
| 7,255,678 | B2 | 8/2007 | Mehi et al. |
| 7,275,439 | B2 | 10/2007 | Zagzebski et al. |
| 2004/0019318 | A1* | 1/2004 | Wilson et al. ............. 604/22 |
| 2005/0272975 | A1* | 12/2005 | McWeeney et al. ........ 600/113 |
| 2006/0241465 | A1* | 10/2006 | Huennekens et al. ....... 600/458 |
| 2008/0009745 | A1 | 1/2008 | Hossack et al. |
| 2008/0214937 | A1 | 9/2008 | Kim |

FOREIGN PATENT DOCUMENTS

| | | |
|---|---|---|
| JP | 2001-327499 | 11/2001 |
| JP | 2008510654 | 4/2008 |
| JP | 2008168490 | 7/2008 |
| WO | WO 94/16625 | 8/1994 |
| WO | WO 2007/115307 A2 | 10/2007 |

OTHER PUBLICATIONS

Patent Cooperation Treaty—Korean Intellectual Property Office, International Search Report for International Application No. PCT/US2009/069787, mailed Jul. 27, 2010, 3 pages.

Japanese Patent Office, JP Office Action dated May 26, 2015, for Application No. 2011-545371, 8 pages (including English translation).

European Patent Office, European Office Action dated Sep. 20, 2016, for Application No. 09838026.4, 5 pages.

* cited by examiner

ULTRASOUND CATHETER WITH ROTATABLE TRANSDUCER

CROSS-REFERENCE TO RELATED APPLICATIONS

This application is a continuation of U.S. patent application Ser. No. 12/351,368 filed on Jan. 9, 2009, which is hereby incorporated by reference in its entirety.

FIELD OF THE INVENTION

The present invention generally relates to ultrasound catheters. More specifically, the present invention pertains to an ultrasound catheter having a rotatable transducer element that provides a forward looking view in intracardiac or intravascular diagnostics.

BACKGROUND OF THE INVENTION

The development of new medical technologies and equipment has provided an increasing number of options available to doctors for the diagnosis and treatment of cardiovascular diseases. For example, ultrasound imaging technologies have enabled doctors to create and view a variety of images generated by one or more sensors inserted within a vasculature.

One ultrasound imaging technology that has been employed is intravascular ultrasound (IVUS). In IVUS imaging systems, an ultrasonic transducer assembly is attached to a distal end of a catheter. The catheter is carefully maneuvered through a patient's body, usually over a guide wire, to an area of interest such as within a coronary artery. The transducer assembly transmits ultrasound waves and receives echoes from those waves. The received echoes are then converted to electrical signals and transmitted to processing equipment where, for example, an image of the area of interest may be displayed.

Intracardiac echocardiography (ICE) is yet another imaging technology that has been used. ICE is similar to IVUS in that it uses a catheter with a transducer assembly at its distal end to facilitate imaging. However, ICE involves maneuvering the tip of the catheter, and hence transducer assembly, into the heart so that the walls of a heart chamber can be imaged. ICE catheters also typically include a steering mechanism that permits articulation of the distal end of the catheter.

IVUS and ICE catheters are relatively small because they need to be capable of traversing the inside of an artery. Consequently, the transducer assembly needs to be correspondingly small, while at the same time constructed to provide an imaging area that is as large as possible.

One known way to construct an ultrasound imaging catheter is to utilize a side firing element or array at the distal end of the catheter wherein the array is rotated about the longitudinal axis of the catheter. Another way is to arrange an array of transducer elements circumferentially around the longitudinal axis of the catheter. Yet another way is to arrange a linear array of transducer elements along the longitudinal axis of the catheter body. However, such arrangements typically provide a side looking view and it is not possible to view the area in front of the catheter assembly. In addition, implementations that utilize an array typically require additional circuitry to control multiple transducer elements.

BRIEF SUMMARY OF THE INVENTION

An ultrasound catheter assembly having a rotatable transducer assembly is disclosed. The ultrasound catheter assembly includes an elongate flexible shaft having a lumen and a proximal end and a distal end. A collar is coupled to the distal end. The transducer assembly, comprising a transducer element and transducer housing, is rotatably mounted within the collar. The catheter assembly further includes a drive member that traverses the length of the flexible shaft and engages the transducer housing. Rotation of the drive member in a first direction causes the transducer housing to rotate in an oscillatory fashion in a second direction.

BRIEF DESCRIPTION OF THE SEVERAL VIEWS OF THE DRAWINGS

The various features of the present invention and the manner of attaining them will be described in greater detail with reference to the following description, claims, and drawings, wherein reference numerals appear in more than one drawing, where appropriate, to indicate a correspondence between the referenced items, and wherein:

It should be understood that the sizes of the different components in the figures may not be in proportion and are shown for visual clarity and for the purpose of explanation.

DETAILED DESCRIPTION OF THE INVENTION

The following embodiments are related to an ultrasound catheter assembly 10. For the purpose of illustration, the ultrasound catheter assembly 10 is described in the context of an ultrasound catheter system for use as an intracardiac echocardiography (ICE) catheter or an intravascular ultrasound (IVUS) catheter. However, it will be understood that other applications of the disclosed catheter assembly are contemplated for alternative embodiments. For example, the disclosed ultrasound catheter can be used in any application where it is desirable to image a chamber or cavity that is accessible via a lumen.

Figure 1:
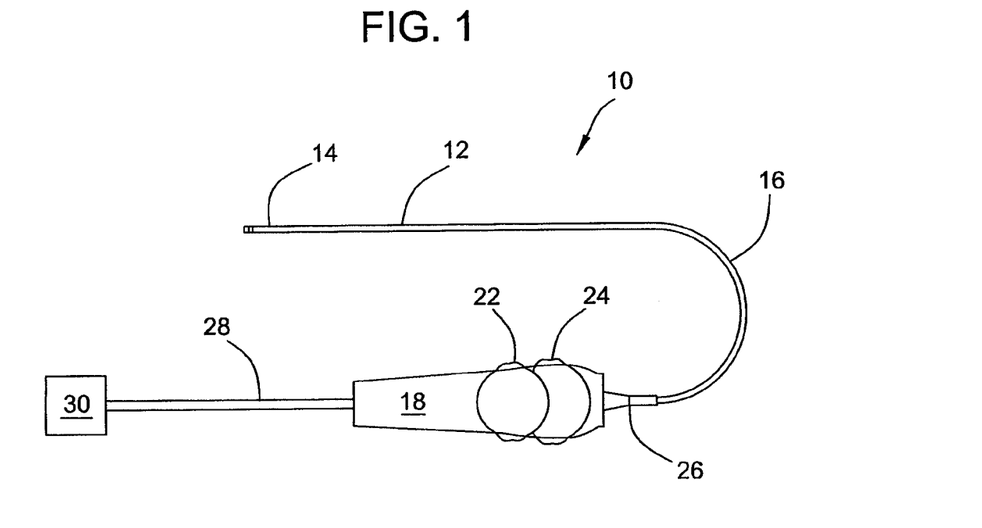
FIG. 1 is an illustration of an ultrasound catheter.

FIG. 1 illustratively depicts an embodiment of the catheter assembly 10 including a catheter shaft 12. The catheter shaft 12 is a generally flexible elongate member having a distal segment 14 and a proximal segment 16. The proximal segment 16 is optionally attached to a handle 18. The handle 18 may include a motor assembly arranged to rotate a drive member and/or incorporate one or more actuators for steering the catheter in accordance with the description that follows.

Also shown is a connector 30 and cable 28. The cable 28 connects the connector 30 to the handle 18. The connector, which can be any of many possible configurations, is used to interconnect the catheter assembly 10 with an ultrasound system for processing, storing, manipulating and displaying data obtained from signals generated by a transducer assembly mounted at the distal segment 14 of the catheter assembly.

Figure 2:
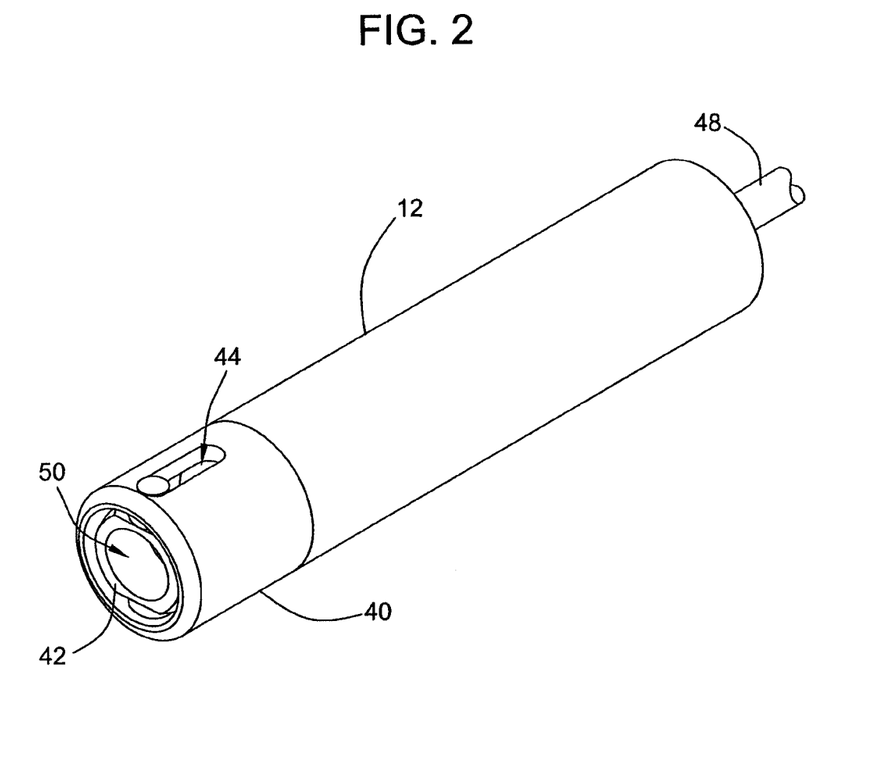
FIG. 2 is an illustration of the distal end of the ultrasound catheter.

FIG. 2 illustrates the distal end of the catheter assembly 10 which includes a rotatable transducer assembly. As shown, a collar 40 is connected to the catheter shaft 12. The collar 40 can be connected to the catheter shaft in any suitable manner, such as glued, pressure fit and the like.

Disposed generally within the collar 40 is a transducer housing 42. As will become more apparent from the description that follows, the transducer housing 42 is arranged such that it may pivot about an axis that is substantially transverse to the longitudinal axis of the catheter shaft 12.

In the embodiment shown in FIG. 2, the collar 40 includes a slotted portion 44 that receives a portion of the transducer housing 42. It will be understood that a slotted configuration is only one possible configuration for receiving a portion of the transducer housing. For example, instead of the slotted portion 44, the collar 40 may include a hole or any other shape suitable to receive a corresponding reciprocal portion of the transducer housing 42.

The catheter assembly 10 further includes a drive member 48. Drive member 48 is disposed within the catheter body and is adapted to rotate along an axis parallel with the longitudinal axis of the catheter shaft. Rotation of the drive member 48 causes the transducer housing 42 to rotate in an oscillatory manner about the transverse axis of the catheter.

The catheter shaft 12, collar 40, and transducer housing 42 are made of any suitable material. An example of a material suitable for the catheter shaft is engineered nylon (such as Pebax® polyether block amide) and includes a tube or tubing, alternatively called a catheter tube or tubing. An example of a material suitable for the collar and transducer housing is stainless steel and/or other material capable withstanding the forces created by oscillatory movement of the transducer housing.

The transducer housing 42 includes a chamber 50. The chamber 50 houses one or more transducer elements which are cable of transmitting ultrasonic waves, receiving echoes from the ultrasonic waves, and converting the waves into electrical energy. The structure of ultrasound transducer elements used in catheter assemblies is well known in the art and, therefore, not described in detail herein. Briefly, however, a transducer element generally comprises a cuboid (or other suitable shape) of piezoelectric material that is sandwiched between a pair of conducting electrodes. The transducer element also preferably includes a backing material of such type and characteristic as to minimize the effects of ringing through absorption and/or scattering of spurious echoes. An example of the types of transducer elements that can be used with the present invention are described in Eberle et al., U.S. Pat. No. 5,368,037 assigned to the same assignee of the present invention.

Figure 3:
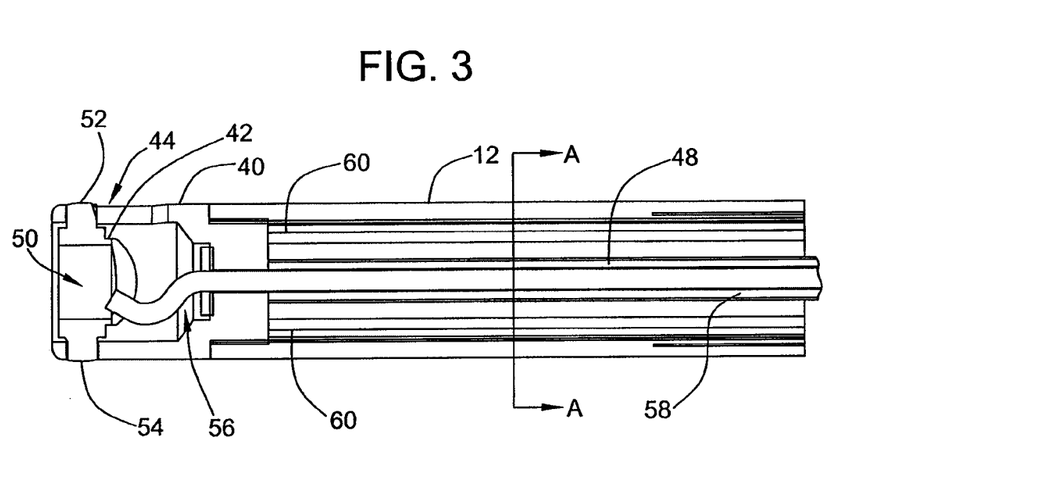
FIG. 3 is a cross-section taken along the longitudinal axis of the catheter.

FIG. 3 illustrates a cross sectional view of the distal end of the catheter assembly 10. The transducer housing 42 includes upper pin 52 and lower pin 54. The upper pin 52 is received in slot 44 of collar 40 and the lower pin 54 is received within a reciprocal circular opening in the collar 40. A function of the slot is to facilitate manufacture of the device and more particularly insertion of the transducer housing 42 into the collar 40. In this regard, the housing 42 may be placed in the collar 40 at an angle with the pin 54 being placed in the reciprocal hole. The pin 52 freely translates along the slot 44 as the housing 42 is placed in a final upright position.

As previously described, the slot 44 is optional and other arrangements such as a second reciprocal hole may be used. Where a reciprocal hole or other arrangement is used, it may be beneficial to provide other mechanisms to facilitate device construction. For example, one or both of pins 52 or 54 may be made of flexible or semi-flexible material so that they may be deformed while the transducer housing 42 is placed in the collar 40.

As shown in FIG. 3, an interior wall of the transducer housing 42 defines the chamber 50. The chamber is depicted as generally cylindrical in overall shape. However, it will be understood by those of skill in art that the inside wall can be shaped and arranged to define a chamber suitable to accommodate the shape and arrangement of the particular transducer element(s) used.

The drive member 48 has a proximal and distal end and generally traverses a central longitudinal axis of the catheter body 12. The distal end of the drive member 48 includes a cam portion 56 that, at least in part, engages the transducer housing 42 as described herein below. In the embodiment shown, the cam portion 56 is non-linear relative to other portions of the drive member 48. The engagement between the drive member and transducer housing is such that rotation of the drive member causes the transducer housing to rotate in an oscillatory manner about an axis that is substantially transverse to the longitudinal axis of the catheter.

The proximal end of the drive member 48 is coupled to a motor (not shown) or other component that is capable of imparting rotation to the drive member 48. The motor may be included in the optional handle 18 (FIG. 1). Alternatively, the motor is a separate component.

In an embodiment of the invention, the catheter assembly 10 includes a guide 58 having a lumen therethrough. The drive member 48 is disposed within the lumen of the guide 58.

The drive member 48 may be made of any suitable flexible material. For example, the drive member 48 may be made of stainless steel. In an embodiment of the invention, the cam portion 56 of the drive member is coated with Teflon or other lubricious material. The guide 58 may be formed from any suitable material and may be lubricious to minimize friction with the drive member 48 and to facilitate rotation of the drive member. Examples of suitable materials include plastic, Pebax®, Fluorinated Ethylene Propylene (FEP) or Teflon®.

FIG. 3 further illustrates one or more optional pull tendons 60 within the catheter assembly. When used, the pull tendons 60 (also called a steering wire or steering line) allow the distal end of the catheter to be articulated. A distal end of each pull tendon 60 is anchored to the distal end of the catheter body 12. For example, the distal end of the pull tendon 60 is affixed to the collar 40. The proximal end of the pull tendon 60 is connected to handle 18. One or more of actuators 22, 24 are used to pull the pull tendons 60 which causes the catheter to bend in a desired way. The handle 18 and actuators 22, 24 are described in further detail in U.S. patent application Ser. No. 11/696,573 entitled "Ultrasound Catheter and Hand-Held Device for Manipulating a Transducer on the Cather's Distal End," assigned to the same assignee as the present application, the entire contents of which are expressly incorporated by reference.

The pull tendons 60 are made of any suitable material that is of sufficient strength to withstand the pull forces initiated by actuators 22 and 24, while at the same time flexible enough to bend with the catheter body 12. Examples of suitable materials for the pull tendons 60 are metal (e.g. stainless steel, nitinol or other titanium alloy) or non-metal (e.g. aramid fiber such as Kevlar®) or other high tensile types of materials.

Figure 4:
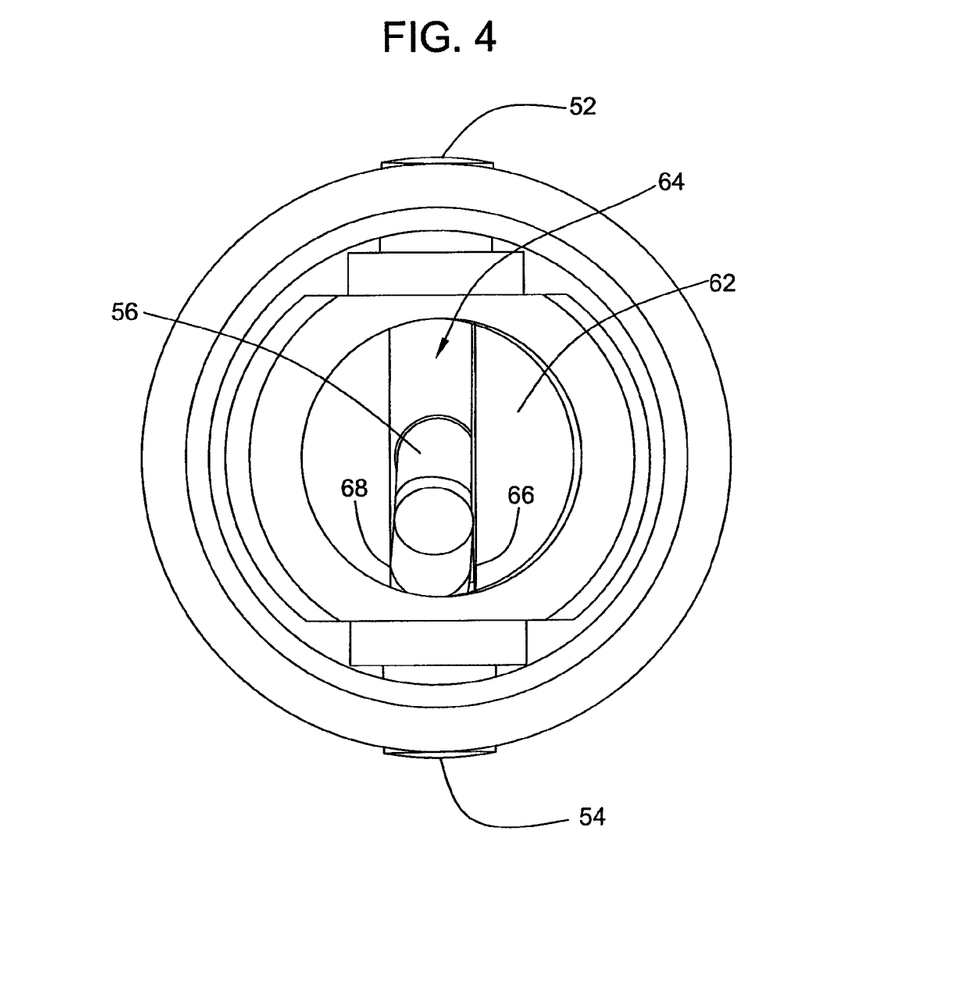
FIG. 4 is a front view of the ultrasound catheter.

FIG. 4 illustrates a front view of the distal end of the catheter assembly 10. As shown, a wall 62 of the transducer housing 42 includes an opening 64. The cam portion 56 of the drive member 48 extends at least partially into the opening 64. In the embodiment shown, the opening is slotted. However, it will be appreciated by those skilled in art that other shapes and arrangements of the opening may be employed.

In operation, the cam portion 56 rotates along with the remaining portion of the drive member 48. As the cam portion 56 rotates, it engages a first wall 66 that partially defines slot 64 thereby causing the transducer housing to rotate in a first direction about an axis generally defined by pins 52 and 54 and transverse to the longitudinal axis of the catheter shaft 12. Corresponding rotation of the transducer element also occurs. At approximately 90 degrees of rotation relative to the position of the cam 56 in FIG. 4, the transducer housing 42 reaches maximum rotation in a first direction. The amount of rotation can be varied by adjusting the geometry of the slot 64 and cam portion 56. For example, the configuration depicted in FIGS. 3-4 results in rotation of about 45 degrees in the first direction. As the drive member 48 rotates between 90 and 180 degrees, the transducer housing rotates back toward a central position as generally shown in FIG. 4.

As the drive member 56 rotates between 180 and 270 degrees, the cam 56 engages a second wall 68 that also partially defines slot 64. This engagement causes the transducer housing 42 to rotate in a second direction that is opposite the first direction. Maximum rotation in the second direction occurs at 270 degrees. Again, the amount of rotation can be varied. However assuming symmetry in the size and arrangement of the cam 56 and opening 64, the amount of rotation in the first and second direction should be substantially the same. As the drive member rotates between 270 and 360 degrees, the transducer housing returns to the central position. The total rotation of the transducer housing is thus about 90 degrees in the embodiment shown.

As will be appreciated from the foregoing description, rotation of the drive member 48 causes the transducer assembly to rotate along the transverse axis in an oscillatory back and forth manner. While this occurs, the transducer element in the transducer housing is activated to emit ultrasound waves and to receive the echoes from the ultrasound waves at a desired rate. For example, at 900 RPM of the drive member 48, the ultrasound transducer element is activated to provide data for about 30 frames of images per second in a generally forward looking direction.

Figure 5:
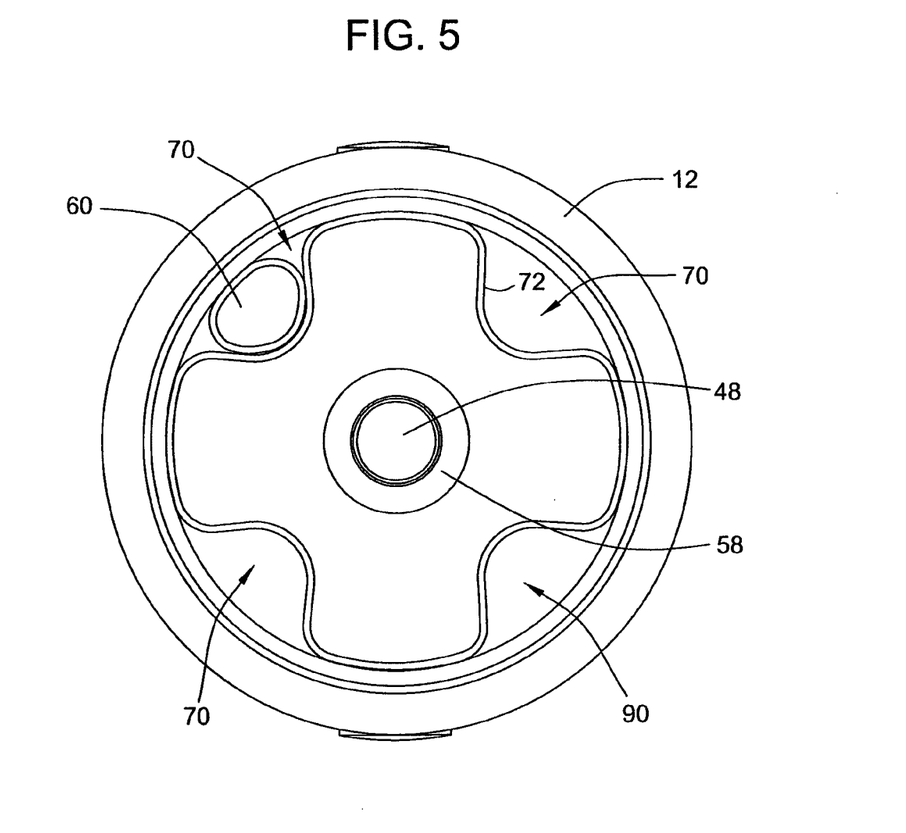
FIG. 5 is a cross-section taken along a transverse axis of the catheter.

FIG. 5 illustrates a cross section of the catheter assembly taken along line A-A (FIG. 3). As shown, the drive member 48 is disposed within the guide 58. The guide 58 and drive member 48 are generally centrally disposed within the catheter shaft 12. The catheter assembly 10 also includes structure 72 which defines one or more lumens 70. The pull tendons 60 are disposed in the one or more lumens along substantially the length of the catheter body 12. Alternatively, the pull tendons can be embedded within the catheter body 12.

Those skilled in the art will appreciate that an electrical connection needs to be provided between the transducer assembly and cable 28 to carry the signals which power and activate the one or more transducer elements and to carry signals representative of received echoes to signal processing equipment. The electrical connection within the catheter assembly needs to robust enough to withstand the oscillatory movement of the transducer housing; while also being flexible. Examples of a suitable electrical connection include coiled wire. As another example, a flexible substrate having conductors disposed thereon can be used.

The catheter assembly 10 may include an additional lumen that runs inside the catheter body 12 substantially parallel to guide 58. The additional lumen can be used to deliver a therapeutic device or fluid to the isonated field to facilitate image guided therapies or treatments. For example, a therapeutic device such as a laser fiber-bundle can be used to treat tissue (e.g. an uncrossable arterial occlusion) ahead of the catheter tip either by tissue ablation, or, tissue photochemotherapy. The laser pulses may be timed with the ultrasound transmit-receive process so that the high frequency laser induced tissue reverberations can be seen in the ultrasound image plane simultaneously. In this way, the invention can dynamically guide the operator's vision during a microsurgical procedure.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Systems and their associated components have been described herein above with reference to exemplary embodiments of the invention including their structures and techniques. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

The invention claimed is:

1. A method of imaging, comprising:
   obtaining an ultrasound catheter assembly comprising:
      an elongate flexible member having a lumen, a proximal end, and a distal end;
      a collar coupled to the distal end of the elongate flexible member, wherein the collar includes an elongated opening and a circular opening extending through the collar opposite the elongated opening;
      a transducer housing rotatably mounted to the collar such that the transducer housing is configured to pivot about an axis transverse to a longitudinal axis of the lumen, a proximal portion of the transducer housing having a slot defined by a first wall portion and an opposing second wall portion, wherein the transducer housing includes a first pin and a second pin opposite the first pin, wherein the first pin is received within the elongated opening of the collar and the second pin is received within the circular opening of the collar, wherein the first pin is translated along the elongated opening of the collar from an insertion orientation extending at an oblique angle with respect to the longitudinal axis of the lumen to an assembled orientation extending transverse to the longitudinal axis of the lumen such that the housing is configured to pivot about an axis transverse to the longitudinal axis of the lumen;

at least one transducer element mounted in the transducer housing;

a drive member extending within the lumen, the drive member comprising an elongated shaft having a bent distal portion defining a cam, the cam of the drive member engaged with the slot of the transducer housing such that rotation of the drive member about the longitudinal axis causes the transducer housing to rotate along the axis that is transverse to the longitudinal axis of the lumen through alternating interactions of the cam with the first and second wall portions defining the slot; and at least one tendon extending along the length of the elongate flexible member for moving a distal portion of the ultrasound catheter assembly in at least one direction; introducing the distal portion of the ultrasound catheter assembly into a vessel of a patient and causing rotation of the drive member to pivot the transducer housing about the axis transverse the longitudinal axis of the lumen to obtain an image.

2. The method of claim 1, wherein causing rotation of the drive member includes utilizing a motor.

3. The method of claim 2, wherein the motor is coupled to a proximal portion of the drive member.

4. The method of claim 1, wherein the drive member of the ultrasound catheter assembly is formed of a flexible material.

5. The method of claim 4, wherein the flexible material is stainless steel.

6. The method of claim 1, further comprising:

steering the distal portion of the ultrasound catheter assembly to a desired location within the vessel.

7. The method of claim 6, wherein the ultrasound catheter assembly includes a handle having at least one steering actuator.

8. The method of claim 7, wherein the at least one steering actuator is coupled to the at least one tendon extending along the length of the elongate flexible member.

9. The method of claim 8, wherein the handle includes at least two steering actuators, a first of the steering actuators coupled to a first tendon extending along the length of the elongate flexible member and a second of the steering actuators coupled to a second tendon extending along the length of the elongate flexible member.

10. The method of claim 9, wherein the first steering actuator and the first tendon control movement of the distal portion of the ultrasound catheter assembly in a first direction and wherein the second steering actuator and the second tendon control movement of the distal portion of the ultrasound catheter assembly in a second direction.

11. The method of claim 6, wherein the distal portion of the ultrasound catheter assembly is configured for intravascular ultrasound.

12. The method of claim 1, wherein the at least one transducer element provides a generally forward looking view in response when pivoting about the axis transverse the longitudinal axis of the lumen.

13. The method of claim 12, wherein the forward looking view is approximately ±45 degrees relative to the longitudinal axis.

14. The method of claim 1, further comprising advancing the distal portion of the ultrasound catheter assembly to a desired location within a heart.

15. The method of claim 14, wherein the desired location within the heart is a particular heart chamber.

16. The method of claim 14, wherein the distal portion of the ultrasound catheter assembly is adapted for intracardiac echocardiography.

17. The method of claim 1, further comprising delivering a therapy to a patient via the ultrasound catheter assembly.

18. The method of claim 17, wherein the therapy is delivered through a further lumen of the elongate flexible member.

* * * * *